(12) United States Patent
Schonenberger et al.

(10) Patent No.: US 10,130,805 B2
(45) Date of Patent: Nov. 20, 2018

(54) WOUND HEALING ELECTRODE SET

(71) Applicant: EMPI, INC., Vista, CA (US)

(72) Inventors: Klaus Schonenberger, Vufflens-la-Ville (CH); Valere Vriz, Montaigu (FR)

(73) Assignee: Empi, Inc., Vista, CA (US)

(*) Notice: Subject to any disclaimer, the term of this patent is extended or adjusted under 35 U.S.C. 154(b) by 185 days.

(21) Appl. No.: 14/929,026

(22) Filed: Oct. 30, 2015

(65) Prior Publication Data
US 2016/0184575 A1 Jun. 30, 2016

Related U.S. Application Data

(63) Continuation of application No. 12/601,459, filed as application No. PCT/IB2008/052048 on May 23, 2008, now Pat. No. 9,174,042.

(30) Foreign Application Priority Data

| May 25, 2007 | (EP) | 07108979 |
| Jun. 21, 2007 | (EP) | 07110731 |
| Apr. 4, 2008 | (EP) | 08154098 |

(51) Int. Cl.
*A61N 1/04* (2006.01)
*A61N 1/20* (2006.01)
*A61N 1/32* (2006.01)

(52) U.S. Cl.
CPC ......... *A61N 1/0468* (2013.01); *A61N 1/0428* (2013.01); *A61N 1/0456* (2013.01); *A61N 1/0476* (2013.01); *A61N 1/0492* (2013.01); *A61N 1/205* (2013.01); *A61N 1/0472* (2013.01); *A61N 1/0484* (2013.01); *A61N 1/326* (2013.01)

(58) Field of Classification Search
CPC .. A61N 1/0412–1/0456; A61N 1/0464; A61N 1/0468; A61N 1/0476; A61N 1/0492; A61N 1/0496; A61N 1/18; A61N 1/20; A61N 1/205; A61N 1/30; A61N 1/303;
(Continued)

(56) References Cited

U.S. PATENT DOCUMENTS 4,381,012 A 4/1983 Russek
4,381,789 A * 5/1983 Naser ................. A61B 5/04085
607/148

(Continued)

FOREIGN PATENT DOCUMENTS

DE 19809218 9/1999
EP 0367320 5/1990
(Continued)

OTHER PUBLICATIONS

Morris, "Product Review, Bio-electrical stimulation therapy using POSiFECT ® rd," Wounds UK, 2:4, 112-116 (p. 15 not included in document) (2006).
(Continued)

*Primary Examiner* — Kami A Bosworth
(74) *Attorney, Agent, or Firm* — Knobbe, Martens, Olson & Bear, LLP

(57) ABSTRACT

The set for the electrical stimulation of a patient, comprises a backing, at least one electrically active zone and a wire connected to said electrically active zone for connection to a stimulator. Said backing has the shape of a bandage or of a plaster.

17 Claims, 4 Drawing Sheets

(58) Field of Classification Search
CPC ...... A61N 1/32; A61N 1/325–1/36003; A61N 1/36014; A61N 1/36021; A61N 1/36042
See application file for complete search history.

(56) References Cited

U.S. PATENT DOCUMENTS

| | | | |
|---|---|---|---|
| 4,398,545 A | 8/1983 | Wilson | |
| 4,619,252 A | 10/1986 | Ibbott | |
| 4,633,879 A | 1/1987 | Ong | |
| 4,635,641 A | 1/1987 | Hoffman | |
| 4,649,923 A | 3/1987 | Hoffman | |
| 4,664,118 A | 5/1987 | Batters | |
| 4,699,146 A | 10/1987 | Sieverding | |
| 4,763,660 A | 8/1988 | Kroll et al. | |
| 4,846,181 A | 7/1989 | Miller | |
| 4,860,737 A * | 8/1989 | Lang | A61F 13/00034 602/43 |
| 4,895,153 A | 1/1990 | Takeuchi et al. | |
| 4,895,154 A | 1/1990 | Bartekt et al. | |
| 4,919,138 A | 4/1990 | Nordenstroom | |
| 4,976,705 A * | 12/1990 | Aki | A61F 13/02 604/20 |
| 4,982,742 A | 1/1991 | Claude | |
| 5,158,081 A | 10/1992 | McWhorter et al. | |
| 5,218,973 A | 6/1993 | Weaver et al. | |
| 5,341,806 A | 8/1994 | Gadsby et al. | |
| 5,395,398 A | 3/1995 | Rogozinksi | |
| 5,433,735 A | 7/1995 | Zanakis et al. | |
| 5,450,845 A * | 9/1995 | Axelgaard | A61B 5/0408 600/382 |
| 5,487,759 A | 1/1996 | Bastyr et al. | |
| 5,557,263 A | 9/1996 | Fisher et al. | |
| 5,607,743 A | 3/1997 | Disselbeck | |
| 5,635,201 A | 6/1997 | Fabo | |
| 5,766,236 A | 6/1998 | Detty et al. | |
| 5,785,040 A | 7/1998 | Axelgaard | |
| 5,814,094 A | 9/1998 | Becker et al. | |
| 5,861,016 A | 1/1999 | Swing | |
| 5,919,155 A * | 7/1999 | Lattin | A61N 1/044 439/909 |
| 6,065,154 A | 5/2000 | Hulings et al. | |
| 6,076,003 A | 6/2000 | Rogel | |
| 6,385,473 B1 | 5/2002 | Haines et al. | |
| 6,411,853 B1 | 6/2002 | Millot et al. | |
| 6,415,169 B1 | 7/2002 | Kornrumpf et al. | |
| 6,611,705 B2 | 8/2003 | Hopman et al. | |
| 6,631,294 B2 | 10/2003 | Andino et al. | |
| 6,861,570 B1 | 3/2005 | Flick | |
| 6,907,294 B2 | 6/2005 | Andino et al. | |
| 7,072,721 B1 | 7/2006 | Trent | |
| 2002/0019652 A1 | 2/2002 | Da Silva et al. | |
| 2002/0094701 A1* | 7/2002 | Biegelsen | B25J 13/084 439/32 |
| 2003/0009122 A1 | 1/2003 | Veras | |
| 2003/0028170 A1 | 2/2003 | Anderson et al. | |
| 2003/0036716 A1 | 2/2003 | Knutson et al. | |
| 2003/0040691 A1 | 2/2003 | Griesbach et al. | |
| 2003/0045825 A1 | 3/2003 | Etheredge | |
| 2003/0050675 A1 | 3/2003 | Nachum | |
| 2003/0059386 A1 | 3/2003 | Sumian et al. | |
| 2003/0097118 A1 | 5/2003 | Zhang et al. | |
| 2003/0105419 A1 | 6/2003 | Edwards | |
| 2003/0118528 A1 | 6/2003 | Walters et al. | |
| 2003/0118631 A1 | 6/2003 | Xing et al. | |
| 2003/0125654 A1 | 7/2003 | Malik | |
| 2003/0133991 A1 | 7/2003 | Monroe et al. | |
| 2003/0135150 A1 | 7/2003 | Kuribayashi et al. | |
| 2003/0147879 A1 | 8/2003 | Ny et al. | |
| 2003/0149393 A1 | 8/2003 | Joshi | |
| 2003/0149394 A1 | 8/2003 | Joshi | |
| 2003/0167073 A1 | 9/2003 | Nakamura et al. | |
| 2003/0170892 A1 | 9/2003 | Boyce | |
| 2003/0176828 A1 | 9/2003 | Buckman et al. | |
| 2003/0191426 A1 | 10/2003 | Lerner et al. | |
| 2004/0015223 A1 | 1/2004 | Andino et al. | |
| 2004/0030267 A1 | 2/2004 | Orten | |
| 2004/0049145 A1 | 3/2004 | Flick | |
| 2004/0080321 A1 | 4/2004 | Reavall et al. | |
| 2004/0143172 A1 | 7/2004 | Fudge et al. | |
| 2004/0143313 A1 | 7/2004 | Chang et al. | |
| 2004/0147977 A1 | 7/2004 | Petrofsky | |
| 2004/0192082 A1* | 9/2004 | Wagner | H05K 1/0283 439/67 |
| 2005/0119715 A1 | 6/2005 | Petrofsky | |
| 2005/0244484 A1 | 11/2005 | Flick | |
| 2005/0283219 A1 | 12/2005 | O'Connor et al. | |
| 2006/0116565 A1 | 6/2006 | Axelgaard | |
| 2006/0173523 A1 | 8/2006 | Rainey et al. | |
| 2006/0189912 A1 | 8/2006 | Garabet | |
| 2007/0088386 A1 | 4/2007 | Babaev | |
| 2008/0027509 A1 | 1/2008 | Andino et al. | |
| 2008/0031934 A1 | 2/2008 | MacPhee et al. | |
| 2008/0119773 A1 | 5/2008 | Flick | |
| 2008/0177219 A1 | 7/2008 | Joshi | |
| 2008/0195018 A1 | 8/2008 | Larson et al. | |
| 2009/0048504 A1 | 2/2009 | Andino et al. | |
| 2009/0048635 A1 | 2/2009 | Andino et al. | |
| 2009/0048651 A1 | 2/2009 | Andino et al. | |
| 2009/0069759 A1 | 3/2009 | Blott et al. | |
| 2009/0177131 A1* | 7/2009 | Dar | A61B 5/1038 602/2 |
| 2010/0056973 A1 | 3/2010 | Farrow et al. | |

FOREIGN PATENT DOCUMENTS

| | | |
|---|---|---|
| WO | WO 1984/01298 | 4/1984 |
| WO | WO 1994/15527 | 7/1994 |
| WO | WO 2001/03768 | 1/2001 |
| WO | WO 2002/068045 | 9/2002 |
| WO | WO 2002/089911 | 11/2002 |
| WO | WO 2004/080534 | 9/2004 |
| WO | WO 2005/096979 | 10/2005 |
| WO | WO 2006/089377 | 8/2006 |
| WO | WO 2008/109058 | 9/2008 |
| WO | WO 2009/083049 | 7/2009 |

OTHER PUBLICATIONS

CUTTING, "Electric stimulation in the treatment of chronic wounds," Wounds UK, 2:1, 1-11 (2006).

* cited by examiner

WOUND HEALING ELECTRODE SET

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57.

TECHNICAL FIELD

The present invention concerns a wound healing electrode set and a device using such an electrode set.

The present invention also concerns an electrode set for an electrically induced wound healing that can be adjusted to the wound size.

BACKGROUND ART

Devices using electrical stimulation for wound healing and also stimulate bone growth are known in the art. For example, the following documents all relate to this field: WO 84/01298, EP 0 367 320, U.S. Pat. No. 4,846,181, U.S. Pat. No. 4,919,138, U.S. Pat. No. 4,982,742, U.S. Pat. No. 5,158,081, U.S. Pat. No. 5,218,973, U.S. Pat. No. 5,395,398, U.S. Pat. No. 5,433,735, U.S. Pat. No. 5,814,094, U.S. Pat. No. 5,861,016, DE 198 09 218, WO 02/068045, U.S. Pat. No. 6,631,294, WO 02/089911, US 2004/0015223, US 2004/0049145, US 2004/0147977, WO 2004/080534, US 2005/0119715, U.S. Pat. No. 6,907,294, WO 2005/096979, US 2005/0244484, US 2006/0173523 and US 2006/0189912.

For example, EP 0 367 320 discloses a system for the treatment of wounds by means of electric stimulation with an electric wound compress, a return electrode, an electric generator and cables for forming electric connections between the elements.

In U.S. Pat. No. 4,846,181, a wound healing device is disclosed using a wound electrode placed preferably at the wound, a dispersive electrode positioned at a distance from the wound and a stimulation unit.

In U.S. Pat. No. 5,218,973, a signal generator provides an electrical output signal and this signal is coupled through a cable, a connector and an active electrode to a soft tissue wound site of a patient. A return electrode engages a separate area of the patient spaced from the wound site and a return path to the generator is provided through another cable.

U.S. Pat. No. 5,861,016 discloses a method for healing a wound of a patient using an electrical stimulator and acupuncture needles. The method involves the step of positioning a plurality of acupuncture needles coupled to the electrical stimulator substantially around the wound. The next step include applying a current to said acupuncture needles.

In U.S. Pat. No. 6,631,294, an electrode system is provided that generates a current flow that envelops and permeates an entire wound site. The electrode system includes two electrodes that are shaped and oriented to cause the current to flow form one electrode through the wound to the other electrode. A first electrode is applied to the wound site and a second electrode encircles the first electrode and is applied to the skin surrounding the wound site.

In WO 2005/096979, the apparatus comprises an array of needles that penetrates the skin and serve as electrodes to deliver radio frequency current or other electrical or optical energy into the tissue being treated, causing thermal damage in controlled patterns.

SUMMARY OF THE INVENTION

It is an aim to improve the known devices for stimulation and treatment of the body of the user, for example the treatment of wounds.

More specifically, it is an aim of the present invention to provide a system and electrodes or electrically active zones that are easy to use.

To this effect, the present invention comprises an electrode set that can be applied to a region of the body of the user, for example a wounded region.

In the present description, the notion of "electrode" should be understood as "electrically active zone" and both notions will be used indifferently in the present application.

Another idea of the present invention is to combine a bandage, such as a spunlace backing, or a plaster (for example a sticking plaster) with at least two electrically active zones that is applicable to the body of a user.

According to the invention, the bandage or plaster can be easily applied directly onto a painful area (for example the ankle, knee or elbow, or any other part of the body) or a wound to be healed. The use of a bandage made of a spunlace backing or a plaster brings a mechanical support to the system and also allows a better application of the active zones against the body of the user.

Of course, the present invention is not limited to a spunlace backing (only given by way of example): any textile that can be used as a bandage can be combined with the electrically active zones according to the teaching of the present invention. For example, bandages can be made from generic cloth strips, to specialized shaped bandages designed for a specific limb or part of the body, i.e. knitted, woven and non-woven material.

Preferably, the bandage used, or at least a part of it, is elastically deformable. Of course, non-elastic bandages might also be used or a combination of both.

In the case of a sticking plaster, any suitable material may be used: woven fabric, plastic, or latex rubber.

The active zones may be electrodes of the "EASY" type, i.e. one support layer with two active zones, but one may also envisage two separate single active zones attached to the backing. An example of an electrode of the "EASY" type mentioned above is disclosed in US application 2006/0116565 in the name of Axelgaard.

The active zones may be attached in many ways to the backing (bandage or plaster): for example by using a Velcro™ system placed on the inner side of the bandage/plaster. One may also directly use the backing fabric present with electrodes and extend said backing to form the bandage. In another variant, the electrically active zones can be glued to or sewn on the backing. Preferably however, the active zones are detachable from the backing to allow a reuse of the elements of the system.

In another embodiment, the electrode set according to the present invention comprises a single patch or plaster with active zones. Said patch can be adjustable to the size of a wound when used on such wound or to the user.

In this case, the patch size can be adapted in one direction or in two directions to the size of the wound or of the user.

Preferably, to this effect, the patch comprises a one-time stretchable material placed between the electrically active zones to allow the size adaptation.

An advantage of the patch according to the present invention is that it can be easily adapted to various wound and/or user sizes.

The advantages of the present invention are numerous. For example, it may be applied directly onto a wound or painful area, allowing a direct electrical treatment (for example transcutaneous electrical nerve stimulation (TENS) or any other as desired). Also, the use of a bandage or a plaster brings mechanical support to the treated body part of the user.

BRIEF DESCRIPTION OF THE DRAWINGS

The present invention will be better understood by the description of several embodiments and of the drawings in which.

DETAILED DESCRIPTION

Figure 1:
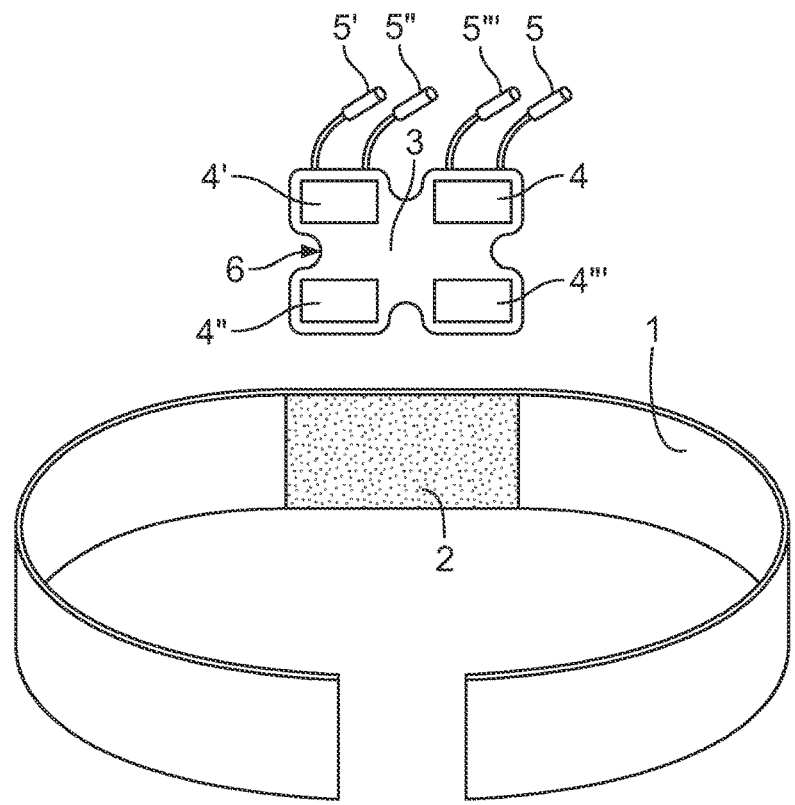
FIG. 1 illustrates a first embodiment of the set according to the invention.
Figure 2:
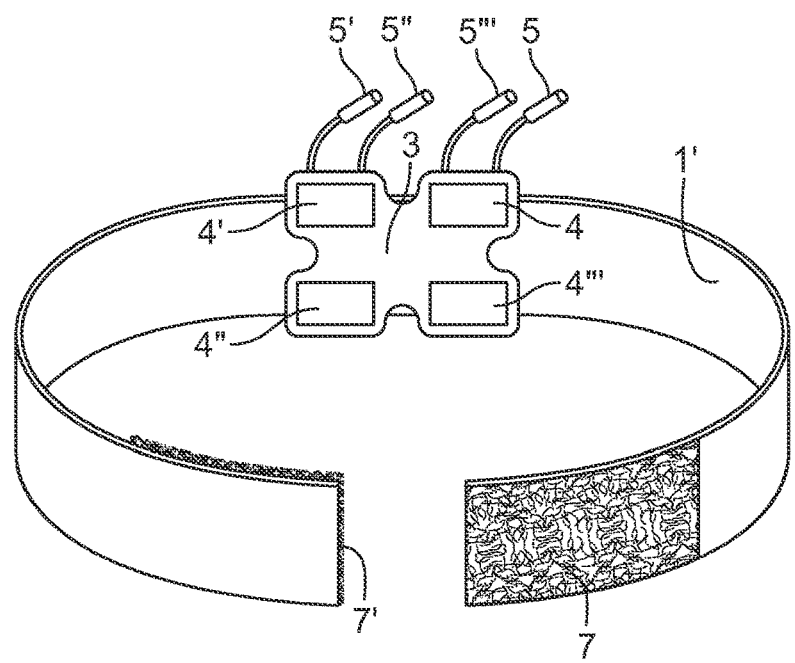
FIG. 2 illustrates a variant of the embodiment of FIG. 1.

A first embodiment is illustrated in perspective in FIGS. 1 and 2. In this embodiment, the set comprises a backing material 1, for example having the shape of a bandage or plaster, said backing having a zone 2 with attachment means, for example a zone comprising Velcro™ or equivalent means. In addition, the set comprises an attachable electrical element 3 which comprises electrically active zones 4, 4', 4", 4''' (for example four as illustrated but this number may be varied if necessary). All said electrically active zones 4-4''' are connected to a wire 5, 5', 5", 5''' for connection to a stimulation device.

The electrical element 3 comprises a zone 6 which corresponds to zone 2 of the backing for attachment of the element 3 to the backing 2, for example as is done with Velcro™. The backing can be used as a bandage and once the electrically active zones are applied to the desired body part of a user, the device can be attached to said part as a bandage, thus maintaining the active zones against the user.

In the variant of FIG. 2 where similar parts are referenced as in FIG. 1, the backing 1' for example has the shape and size of a belt and comprises two additional zones 7, T with attachment means, for example such as Velcro™ for attachment of the backing 1' as a belt. Of course, other equivalent means may be used for attaching the two ends of the backing 1', instead of zones 7, T with Velcro™.

A second embodiment is described with reference to FIGS. 3 to 5. In this variant, the backing material 20 in the shape of a bandage carries two separate electrodes 21, 22, each connected to a connection wire 23, 24. As in the first embodiment, the backing can be made of a spunlace backing, a bandage or any other equivalent material.

Figure 3:
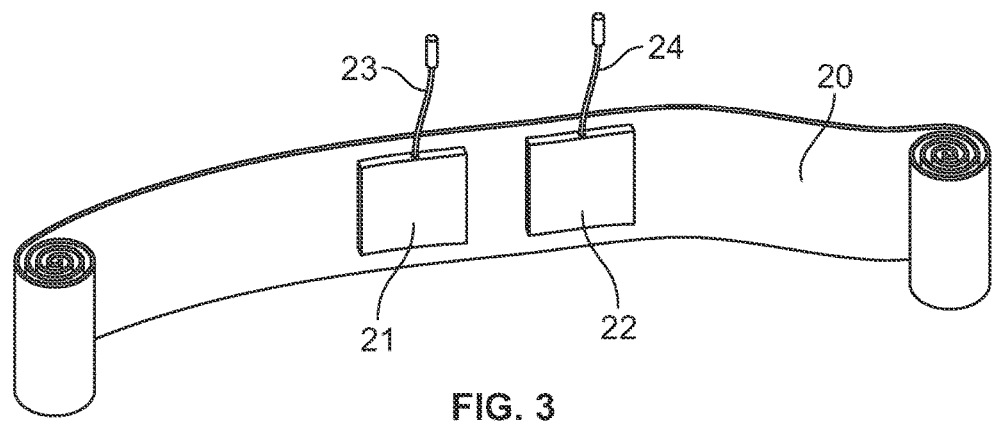
FIGS. 3-5 illustrate a second embodiment and variants therefrom in perspective.
Figure 4:
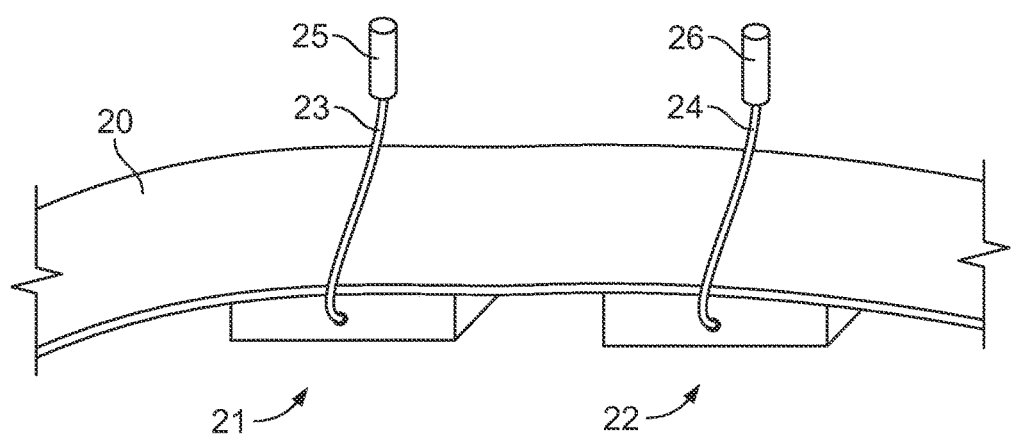

FIG. 4 illustrates a top perspective view of the set of FIG. 3 and the same elements are referenced with the same numbers. In addition, in this figure, one has represented in more detail connectors 25, 26 that are at the end of wires 23, 24 for connection to a stimulation device (not shown).

Figure 5:
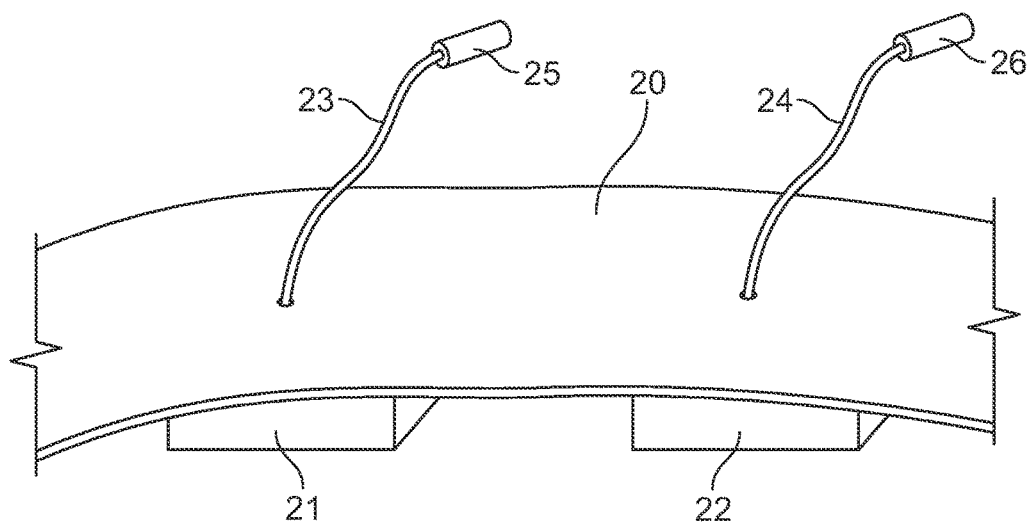

In the variant of FIG. 5, the wires 23, 24 pass through the backing material 20.

Figure 6:
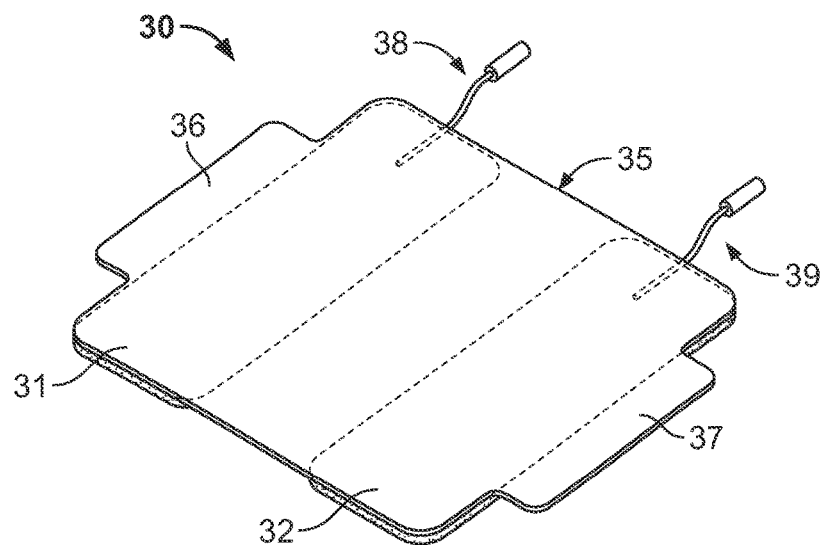
FIGS. 6-7 illustrate a third embodiment in top view and bottom view, respectively
Figure 7:
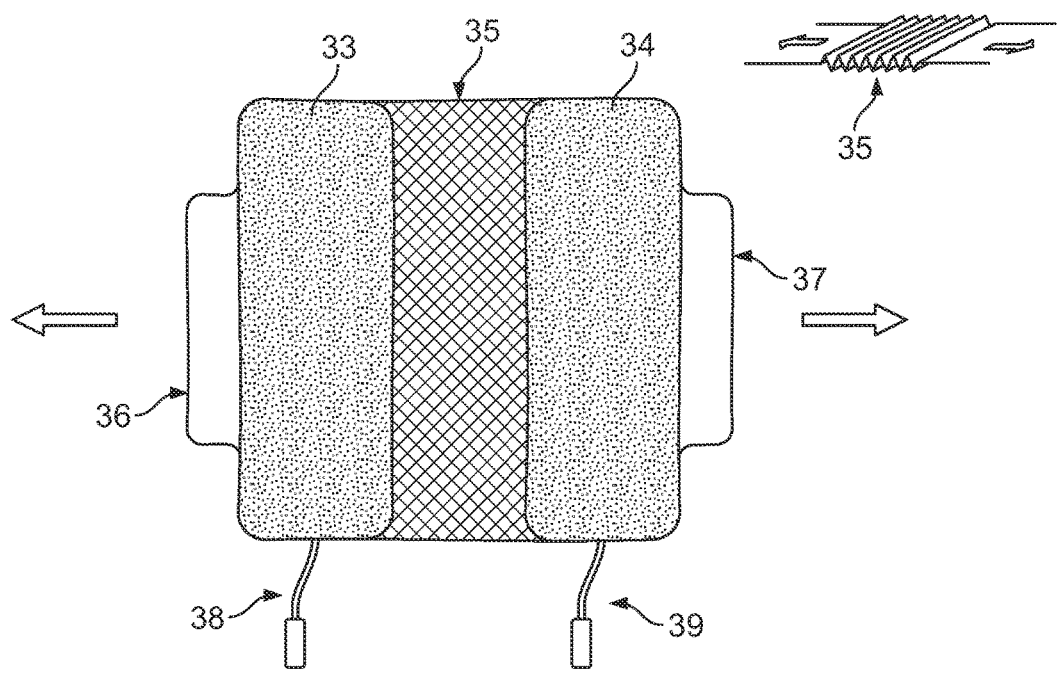

In embodiment illustrated in FIGS. 6 and 7, the backing 30 comprises two lateral zones 31, 32 carrying the electrically active zones 33, 34 and a deformable central zone 35 allowing to adapt the plaster size to the area to be treated, shown also in the detail of FIG. 7.

The deformable zone 35 can be an elastically deformable zone or a "one-time unfold" (i.e. plastically deformable) zone which remains in an unfolded configuration once applied. The elastic zone 35 can be made directly in the backing, for example by cutting said zone into net-shaped zones which can be deformed laterally. This zone 35 can also be made of a specific material with a dedicated shape or by other equivalent means.

Preferably, this embodiment includes at least one lateral flap 36 or 37 which allow a user to pull said flap apart 36 or 37 and thus adapt the size of the plaster to the area on which it is being applied by deformation of the elastic zone. Preferably, it comprises two flaps 36, 37, one on each side of said lateral zones to carry out this "pulling apart" operation. Also, this embodiment includes wires 38, 39 for connection to a device, for example a stimulator. Of course, these wires may comprise connectors for allowing a detachable connection to said device as illustrated in other embodiments of the invention.

Figure 8:
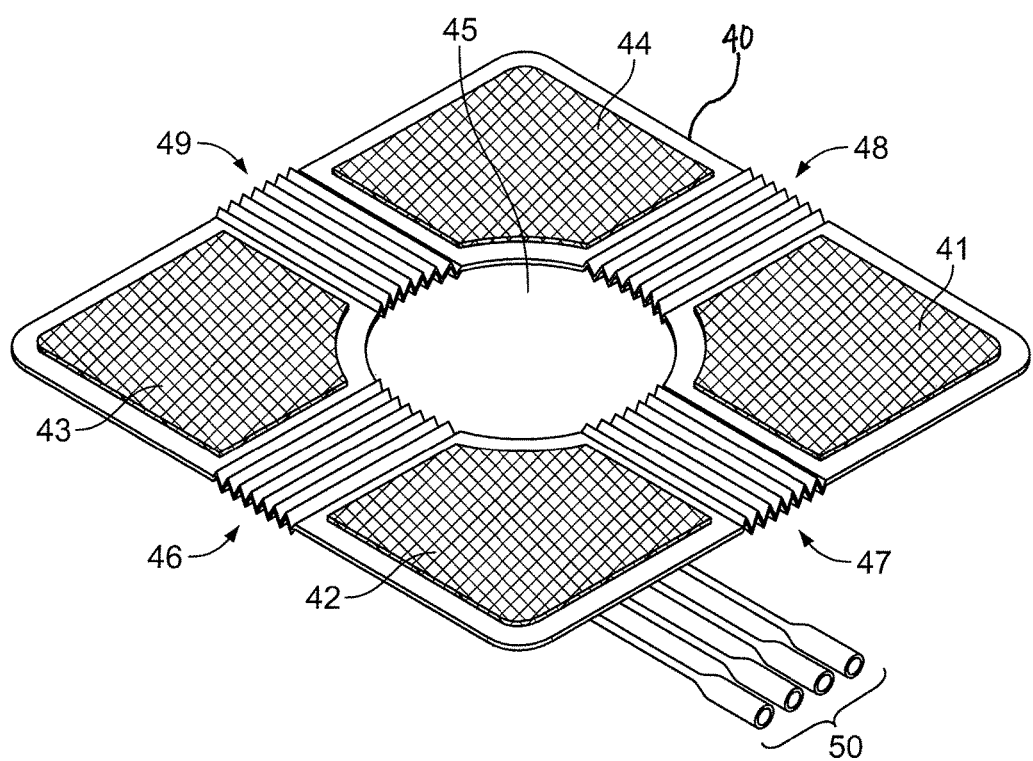
FIG. 8 illustrates a fourth embodiment in bottom view.

A further embodiment of the patch according to the present invention is illustrated in FIG. 8. In this embodiment, the patch comprises a layer of material 40, for example a backing material that is non-conductive.

On this backing, one has placed four electrically active zones 41-44 which form electrodes applied to the user of the patch. As illustrated in FIG. 8, the patch comprises four electrically active zones. Of course, it is possible to use less (for example two) such zones, or more than four zones.

In the centre zone, there is situated an opening 45 for avoiding a wound to be covered by the patch.

Preferably, this backing 40 comprises several parts that are folded 46 to 49 (for example folded zones) and that allow the patch size to be adapted to the wound or to the body of the wearer. Typically, to form these folds 46-49, backing material is made of a one-time stretch material allowing the user to stretch the patch to the proper size and then place said patch without worrying that it will come back to its original size and shape.

In the representation of the FIG. 8, one has illustrated four electrically active zones 41-44 with four folded zones 46-49, but it is also possible with such four electrically active zones to use less than four folded zones, for example only two, preferably zones 46 and 48 or 47 and 49 for symmetry. Of course this is only an example and other configurations are possible.

Also, if less (or more) than four electrically active zones are used, the number of folded zones can be decreased (or increased) accordingly.

On the right side, one has also represented the contacting wires 50 allowing a contact to a stimulator (not shown in this figure), said wires being connected at their other end to the electrically active zones 41 to 44. Of course, in a variant, it is possible to use a single connector in which all the wires are integrated instead of individual wires each with one single connector each.

In the present invention, the electrically active zones may be standard sticky hydrogel electrodes or made of non-sticky material if the set is used with a garment of a bandage allowing the maintain a tight contact between the active zones and the skin.

Various shapes, for the backing, bandage or plaster and also the electrically active zones and the fold zones, may be envisaged and the illustrative example given should not be construed as limiting. For example the shapes could be adapted to the body area on which it will be used.

For the folded zones, instead of one-time stretchable material, one may use a very elastic textile material (for example a spunlace backing with high elasticity).

Preferably, the backing is slightly larger than the electrically active zones to allow a user to hold the set appropriately and stretch it to the right (or desired) size.

When set comprises an opening (such as an opening 45), this allows a wound care even when the set is applied to a patient and without removal of the set.

In a variant, it is possible to use an elastic gauze for protection of the wound for example over or in the opening 45.

In a further variant, it is possible to add an active agent on at least one of the electrically active zones of the embodiments described above to allow the application of medication via iontophoresis.

In another variant, it is possible to add in the opening an elastic electrically conductive gauze. Such a gauze would allow, for example to apply an electric treatment directly into the wound.

Regarding the electrical stimulation, any stimulation may be envisaged. For example, during wound care but not only at this moment, it is possible to apply a TENS waveform to reduce pain. Other signals may be used, for example signals that improve the healing of a wound.

As one will readily understand from the above description, many stimulation signals and method may be carried out with the present set. For example one may apply a TENS stimulation for pain relief. In a variant, one may apply a stimulation that has a wound healing effect. In another variant, one may use the set to carry out a iontophoretic treatment (with the addition of a suitable active agent one at least one electrically active zone).

As one will understand, the active zones of the above described embodiments preferably include each a gel pad for contact with the skin of the user.

The connection wires can pass through the backing/plaster or not. They can be free as represented in the figures or joined in a connector to facilitate the connection and avoid loose single wire. If the connector is asymmetrical, this can ensure that a wrong connection is carried out. Also, to this effect the connector may comprise specific means to ensure a proper and easy connection.

Of course, the embodiments described above are non-limiting illustrative examples and variations with equivalent means are possible. For example, it is possible to use more than two active zones.

The type of active zones used may vary. They can be of the "EASY" type mentioned above, or of another type: for example pads with electrically conductive zones as known in the art.

In addition, other equivalent means than Velcro™ may be used to attach the electrode(s) or pads forming the active zones to the bandage. They can be glued or attached to the bandage by any other equivalent means.

As will be readily understood, the set of the present invention can be used in combination with a electrical stimulator for applying different stimulation to the wearer. Such stimulations can be a TENS stimulation, or an EMS stimulation or any other suitable stimulation applicable with such devices. Typical methods carried out by the present invention can be a healing method using an electrical stimulation. The device according to the invention may also be used for a wound healing method using electrical stimulation or other treatment methods, such a choice being linked to the signal applied to the patient and also to the number and positioning of the electrically active zones. As a skilled worker will understand, many methods are possible.

What is claimed is:

1. An electrostimulation device, comprising:
    a backing having an outside perimeter edge surrounding the backing, the backing comprising
        a first non-conductive deformable zone of the backing having a first edge and a second edge wherein the first non-conductive deformable zone comprises several parts of a material of the backing that are folded between the first and second edges;
        a first lateral zone having an outside edge coextensive with a portion of the outside perimeter edge of the backing and an inside edge coextensive with the first edge of the first non-conductive deformable zone,
        a second lateral zone having an outside edge coextensive with another portion of the outside perimeter edge of the backing and an inside edge coextensive with the second edge of the first non-conductive deformable zone, and
        wherein the first non-conductive deformable zone is located between the first lateral zone and the second lateral zone, the first non-conductive deformable zone being expandable so as to increase a distance between the first lateral zone and the second lateral zone in a first direction; and
    a plurality of electrically active zones located on the backing such that the backing covers one side of each of the plurality of electrically active zones, the plurality of electrically active zones including
        a first electrically active zone located on the first lateral zone, and
        a second electrically active zone located on the second lateral zone.

2. The device of claim 1, wherein the backing further comprises an opening extending through the backing, an edge of the first non-conductive deformable zone and an edge of the first lateral zone each forming a portion of an edge of the opening.

3. The device of claim 2, wherein the first deformable zone is extendable in the first direction, and wherein the backing comprises a second non-conductive deformable zone that is extendable in a second direction, the second direction being different from the first direction, wherein the second non-conductive deformable zone comprises several parts of a material of the backing that are folded.

4. The device of claim 3, wherein the backing further comprises a third non-conductive deformable zone extendible in the first direction and a fourth non-conductive deformable zone extendible in the second direction, the opening separating the first non-conductive deformable zone from the third non-conductive deformable zone, and the opening further separating the second non-conductive deformable zone from the fourth non-conductive deformable zone.

5. The device of claim 4, wherein
    the first electrically active zone is positioned adjacent to the first non-conductive deformable zone and the second non-conductive deformable zone;
    the second electrically active zone is positioned adjacent to the first non-conductive deformable zone and the fourth non-conductive deformable zone; and
    wherein the plurality of electrically active zones further comprise
        a third electrically active zone located on the backing adjacent to the third non-conductive deformable zone and the fourth non-conductive deformable zone, and a fourth electrically active zone located on the backing adjacent to the second non-conductive deformable zone and the third non-conductive deformable zone.

6. The device of claim 4, wherein the first deformable zone and the second deformable zone comprise a one-time stretchable material.

7. The device of claim 6, wherein the one-time stretchable material is plastically deformable.

8. The device of claim 3, wherein the first direction and second direction are substantially perpendicular.

9. The device of claim 2, further comprising a gauze positioned over the opening.

10. The device of claim 9, wherein the gauze is conductive.

11. The device of claim 1, wherein the first deformable zone comprises an elastic material.

12. The device of claim 1, wherein the backing is non-conductive.

13. The device of claim 1, wherein the backing comprises plaster.

14. The device of claim 1, wherein at least one of the plurality of electrically active zones is detachable from the backing.

15. The device of claim 1, wherein at least one of the plurality of electrically active zones comprises an active agent for iontophoretic delivery.

16. The device of claim 1, further comprising a connector for connecting to the plurality of electrically active zones.

17. The device of claim 1, wherein the device is a transcutaneous electrical nerve stimulation (TENS) unit.

* * * * *